(12) United States Patent
Fouillet et al.

(10) Patent No.: US 7,211,223 B2
(45) Date of Patent: May 1, 2007

(54) DEVICE FOR INJECTION AND MIXING OF LIQUID DROPLETS

(75) Inventors: Yves Fouillet, Voreppe (FR); Jean-Luc Achard, Grenoble (FR); Olivier Fuchs, Grenoble (FR)

(73) Assignee: Commissariat A. l'Energie Atomique, Paris (FR)

( * ) Notice: Subject to any disclaimer, the term of this patent is extended or adjusted under 35 U.S.C. 154(b) by 645 days.

(21) Appl. No.: 10/623,617

(22) Filed: Jul. 22, 2003

(65) Prior Publication Data

US 2004/0136876 A1    Jul. 15, 2004

(30) Foreign Application Priority Data

Aug. 1, 2002    (FR) .................................. 02 09822

(51) Int. Cl.
*B01L 3/02* (2006.01)
*G01N 1/10* (2006.01)

(52) U.S. Cl. .................... 422/100; 422/82.01; 436/180
(58) Field of Classification Search ................ 422/100, 422/82.01; 436/180
See application file for complete search history.

(56) References Cited

U.S. PATENT DOCUMENTS

| | | | | |
|---|---|---|---|---|
| 4,659,677 A | | 4/1987 | Glover et al. | |
| 5,486,337 A | * | 1/1996 | Ohkawa | 422/100 |
| 6,149,787 A | * | 11/2000 | Chow et al. | 204/451 |
| 6,713,021 B1 | * | 3/2004 | Shvets et al. | 422/100 |
| 6,787,313 B2 | * | 9/2004 | Morozov et al. | 435/6 |
| 6,918,309 B2 | * | 7/2005 | Brock et al. | 73/863.32 |
| 2001/0041357 A1 | | 11/2001 | Fouillet et al. | |
| 2002/0009392 A1 | * | 1/2002 | Wolk et al. | 422/63 |
| 2003/0148538 A1 | * | 8/2003 | Ng | 436/180 |
| 2004/0101445 A1 | * | 5/2004 | Shvets et al. | 422/100 |
| 2005/0232823 A1 | * | 10/2005 | Brock et al. | 422/100 |
| 2005/0281712 A1 | * | 12/2005 | Williams et al. | 422/100 |

FOREIGN PATENT DOCUMENTS

| | | |
|---|---|---|
| JP | A-06-164497 | 6/1994 |
| JP | A-2000-152026 | 5/2000 |

OTHER PUBLICATIONS

E. Chervenivanova et al.; "On the Deformation of Two Droplets in a Quasisteady Stokes Flow"; Int. J. Multiphase Flow; vol. 11, No. 5; 1985; pp. 721-738; 1985.
Altti Torkkeli et al.; "Droplet Manipulation on a Superhydrophobic Surface for Microchemical Analyis"; Transducers '01 Eurosensors XV; 2001.

* cited by examiner

*Primary Examiner*—Brian R. Gordon
(74) *Attorney, Agent, or Firm*—Oliff & Berridge, PLC

(57) ABSTRACT

The device enables a second drop to be mixed in a first drop deposited on an electrically insulating layer of an analysis support, in a viscous liquid environment and to mix the resulting drop. The device comprises at least one injector forming the second drop above the first drop. After formation of the second drop, a voltage impulse is applied between a first electrode, arranged under the electrically insulating layer of the analysis support, underneath the first drop, and a second electrode arranged near the outlet orifice of the injector. The voltage impulse fosters the coalescence phenomenon between the two drops, while preventing risks of contamination of the injector by the reagent of the first drop.

16 Claims, 8 Drawing Sheets

D

DEVICE FOR INJECTION AND MIXING OF LIQUID DROPLETS

BACKGROUND OF THE INVENTION

The invention relates to a device for injection and mixing of liquid droplets, comprising means for mixing a second drop with a first drop deposited on an electrically insulating layer of an analysis support.

STATE OF THE PRIOR ART

A large number of fields such as biology, chemistry or optics, and in particular chip labs or labs-on-a-chip, require a large number of samples to be prepared and treated then analysed, which means that liquids in small quantities have to be made to flow or to be manipulated. Microfluidics enables, for example, small volumes of liquid to be made to flow in micro-machined channels. Another approach consists in manipulating small droplets of liquid and making them merge, in order for example to mix two different reagents. It is also possible to analyse the drops resulting from this merging.

A very large number of methods exist to manipulate drops of liquid, in particular with electrostatic forces. Thus the article "Electrowetting-based actuation of liquid droplets for microfluidic applications" by. M. G. Pollack et al. (Applied Physics Letters, vol 77, pp 1725–1726, 2000) describes an electrostatic method for displacing droplets based on the electrowetting phenomenon, enabling the surface tension of the droplets to be controlled electrically and the droplets to be moved with voltages of up to 120 Volts. The droplets are placed between two planes containing electrodes covered with an electrically insulating layer, rendered hydrophobic by a deposit of fluorinated polymer of Teflon® type of small thickness. They can be injected between the two planes by stuck capillaries.

The article "Droplets manipulation on a superhydrophobic surface for micro-chemical analysis" by A. Torkkeli et al. (Transducers'01 Eurosensors XV, 10–14 Jun. 2001) describes an open system, the drop 1 being deposited directly on the hydrophobic surface 3 of a wafer 2 (FIG. 1). Several parallel electrodes 4 covered by an insulating layer 5 are placed on the wafer 2, generating electrostatic forces which move the drop 1 horizontally, from one electrode to another in the direction indicated by the arrow in FIG. 2. Drops 1a and 1b can be mixed when their transport paths meet (FIG. 2), thus forming a drop 1c. The drop 1c can in turn meet a drop 1d to form a drop 1e which is separated into two drops 1f and 1g to be analysed. The drops are deposited on the surface 3 by pumping through holes 6 formed in the wafer 2 (FIG. 3). There are then risks of biological contamination of the orifices 6.

OBJECT OF THE INVENTION

The object of the invention is to achieve a device for injection and mixing of droplets, preventing biological contamination of the injection means, while mastering the volumes of drops injected and mixed and preventing evaporation of the drops during the injection and mixing process, which must be reproducible, but also during the analysis process.

According to the invention, this object is achieved by the fact that a viscous liquid in which the first and second drops are not miscible, is deposited on the electrically insulating layer of the analysis support and that the device comprises at least one injector designed to form, at an outlet orifice, the second drop above the first drop, the device comprising control means for controlling a voltage applied between a first electrode, arranged under the electrically insulating layer of the analysis support, underneath the first drop, and a second electrode arranged near to the outlet orifice of the injector.

According to a development of the invention, the electrically insulating layer of the analysis support is arranged on an electrically insulating support provided with an electrically conducting zone forming the first electrode.

It is also an object of the invention to mix the content of the resulting drop.

This object is notably achieved by the fact that the control means comprise means for placing the first and second electrodes at the same potential during formation of the second drop by the injector, and means for applying a first voltage impulse between the first and second electrodes, after formation of the second drop, during a first period of about a few milliseconds to one second.

According to one feature of the invention, the control means comprise means for applying a second voltage impulse between the first and second electrodes, during a second time period of about a few milliseconds to a few seconds after the first impulse.

BRIEF DESCRIPTION OF THE DRAWINGS

Other advantages and features will become more clearly apparent from the following description of particular embodiments of the invention, given as non-restrictive examples only and represented in the accompanying drawings, in which.

DESCRIPTION OF PARTICULAR EMBODIMENTS

The invention consists in making droplets from a few nanolitres to a few microlitres coalesce on an analysis support. As the size of the drops is relatively small, the droplets have to be prevented from evaporating during the injection and mixing process, but also during the analysis process. For this, the droplet injection and mixing process can take place in a viscous liquid environment in which the droplets are not miscible. The viscous liquid can for example be oil, whereas the droplets can be formed by aqueous solutions.

Figure 1:
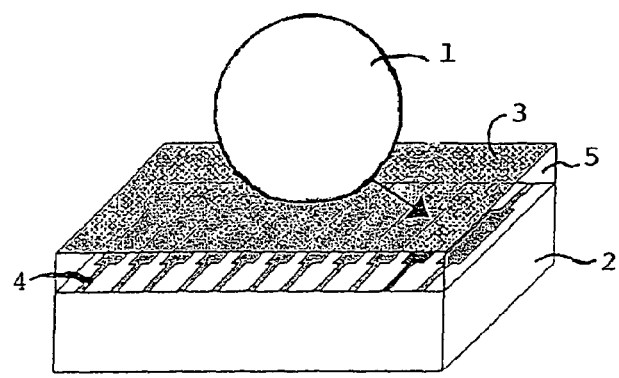
FIGS. 1, 2 and 3 represent a device for movement and mixing of droplets according to the prior art.
Figure 2:
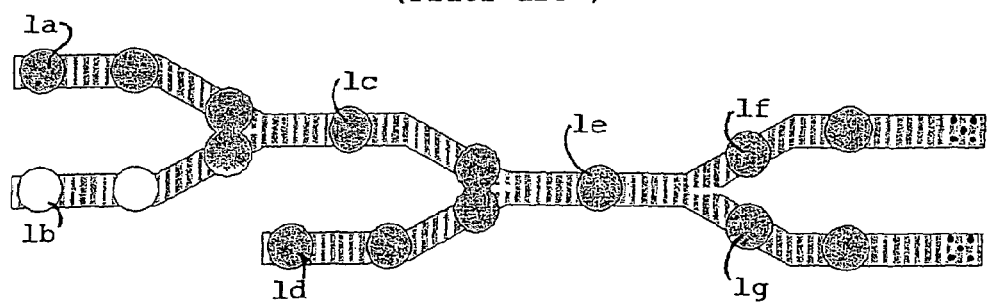
Figure 3:
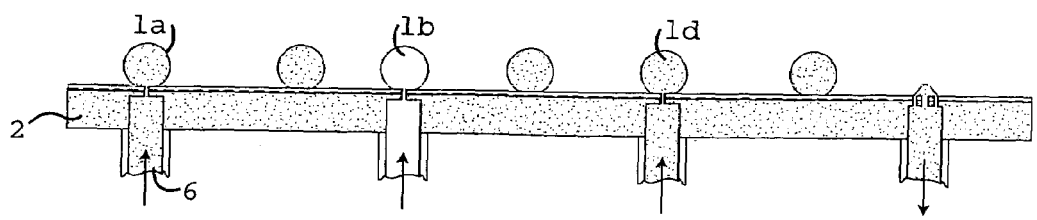
Figure 4:
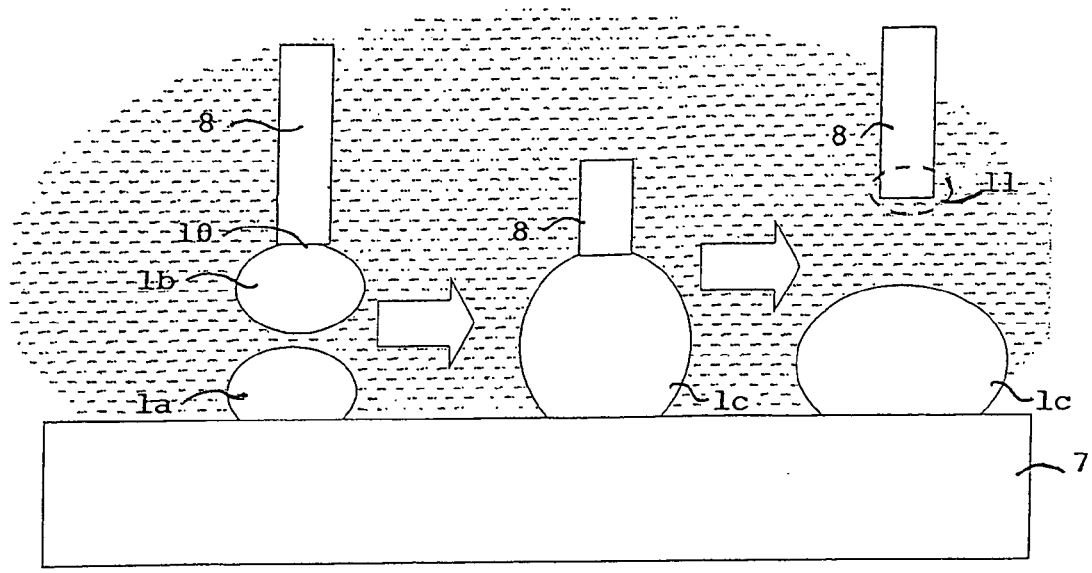
FIG. 4 is a schematic representation of an embodiment of an injection and mixing device.

However the risk of biological contamination when drops are injected is maximum if a drop 1b is simply injected into a drop 1a to form a drop 1c, as represented in FIG. 4. In this case, a first drop 1a is deposited on an analysis support 7. An injector 8 forms a second drop 1b above the first drop 1a, via an outlet orifice 10, so as to make the second drop 1b coalesce with the first drop 1a to form a third drop 1c. If the outlet orifice 10 of the injector is close to the first drop 1a, the third drop 1c can remain in contact with the outlet orifice 10 of the injector 8, after the coalescence phenomenon of the first and second drops 1a and 1b. The outlet orifice 10 is then liable to contain residues 11 of the first drop 1a and therefore to be contaminated, which is liable to contaminate other drops when the injector forms other seconds drops 1b, to be mixed with other first drops 1a.

Figure 5:
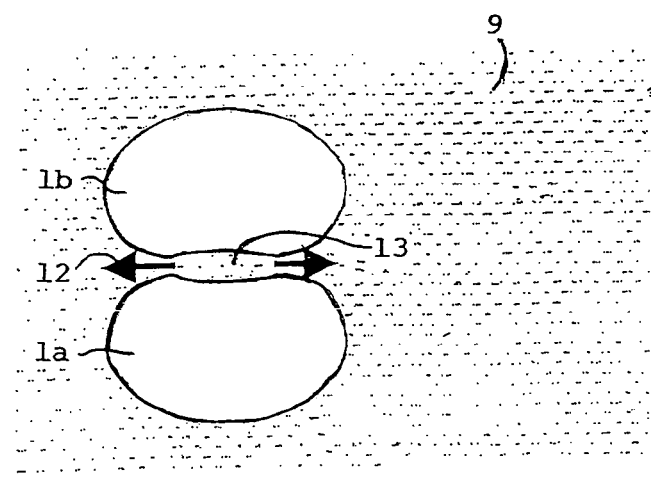
FIG. 5 represents coming into contact of two drops in a viscous liquid environment according to the prior art.

According to the article "On the deformation of two droplets in a quasisteady Stokes flow" by E. Chervenivanova and al. (Int. J. Multiphase Flow, Vol 11, n°5, p721–738, 1985), movement of two drops 1a and 1b towards one another in a viscous liquid environment 9 results in a drainage flow 12 of the viscous liquid environment 9 between the two drops (FIG. 5). The drainage flow 12 is generally too slow compared with the speed of movement of the drops 1a and 1b towards one another of mechanical or gravitational origin, and the latter are consequently deformed. A dimple 13 then appears. This mechanism momentarily opposes coalescence of the drops throughout drainage. The drainage time is longer the more viscous the liquid environment 9. The drainage time therefore varies greatly and can last for more than one minute, rendering the coalescence process hardly reproducible.

The use of known injectors does not enable the drawbacks described above to be overcome. For example, injectors using so-called "electro-spray" methods, which enable very small droplets to be ejected from a nozzle by means of electrostatic forces, cannot be applied in a liquid environment having a non-negligible viscosity.

On the other hand, the device for injection and mixing of liquid droplets according to the invention makes it possible in particular:
1. to achieve the reagent mixture by coalescence of two drops in a relatively viscous liquid environment,
2. for the outlet orifice of the injector not to be contaminated by the reagent forming the first drop 1a,
3. to control the volume of the second drop emitted by the injector,
4. and to achieve a reproducible injection and mixing process.

Figure 6:
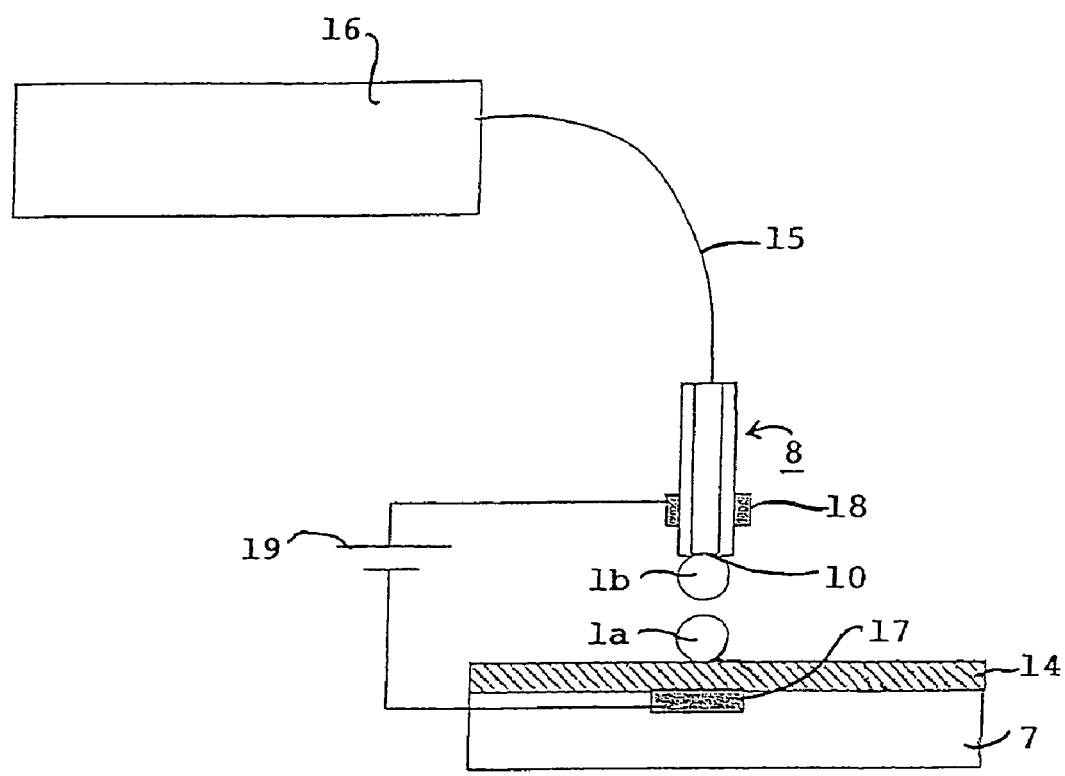
FIG. 6 is a schematic representation of a first embodiment of an injection and mixing device according to the invention.

According to a first embodiment, represented in FIG. 6, the injection and mixing device comprises an analysis support 7 comprising an electrically insulating layer 14 on which a first drop 1a is deposited. An injector 8 designed to form a second drop 1b, via an outlet orifice 10, is connected to a first end of a capillary tube 15, the second end whereof being connected to a volumetric pump 16, containing the reagent constituting the second drop 1b. The injector 8 is arranged above the first drop 1a, so as to make the second drop 1b coalesce with the first drop 1a.

A viscous liquid is previously deposited on the electrically insulating layer 14 of the analysis support 7, so as to prevent evaporation of the drops 1a and 1b during the injection, mixing and analysis process, the first and second drops 1a and 1b being immiscible in the viscous liquid. The drops are, for example, aqueous solutions, whereas the viscous liquid is oil or an organic liquid. The first drop 1a is arranged on the electrically insulating layer 14 by any suitable means, which may, for example, be a capillary or an injector of the type of the injector 8.

The coalescence phenomenon of the drops is fostered by electrostatic forces generated by a first and a second electrode 17 and 18, connected to a voltage generator 19. The first electrode 17 is arranged under the electrically insulating layer 14 of the analysis support 7, so as to be placed underneath the first drop 1a. The second electrode 18 is arranged near to the outlet orifice of the injector, so as to be near to the second drop 1b. In FIG. 6, the second electrode 18 is formed by a conducting material surrounding a part of the walls of the injector 8.

The volumetric pump enables the formation of the second drop 1b at the outlet orifice 10 of the injector 8 to be controlled, the two electrodes being placed at the same potential during formation of the second drop 1b. A first voltage impulse is then applied between the first and second electrodes 17 and 18, during a preset time of about a few milliseconds to one second for example. The voltage may be DC or AC at high frequency, and is about a few tens to a few hundred Volts.

The electrostatic forces involved after formation of the second drop 1b do not influence the volume of the latter. They cause a mutual attraction of the first and second drops 1a and 1b, resulting in transfer of the second drop 1b to the first drop 1a, with immediate coalescence of the two drops (FIGS. 7 and 8).

Figure 7:
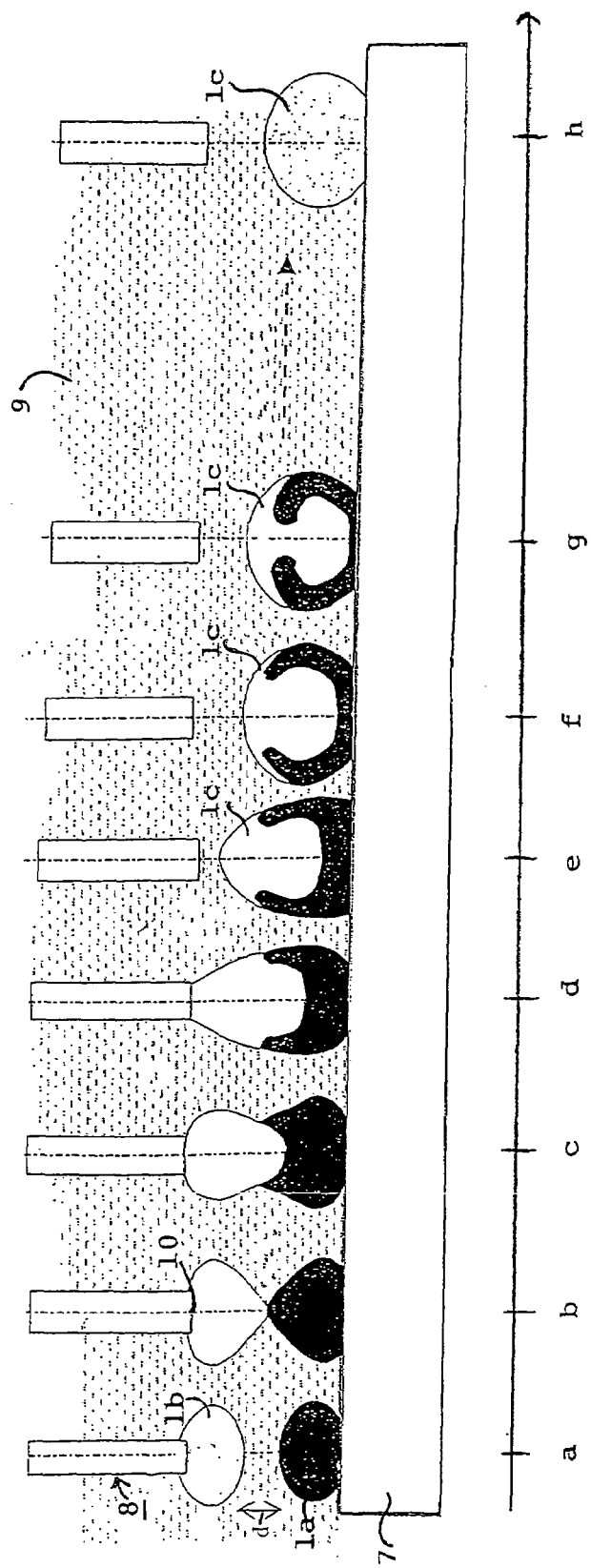
FIGS. 7 and 8 respectively represent the progression versus time of a first and a second mixing process using the device according to FIG. 6.
Figure 8:
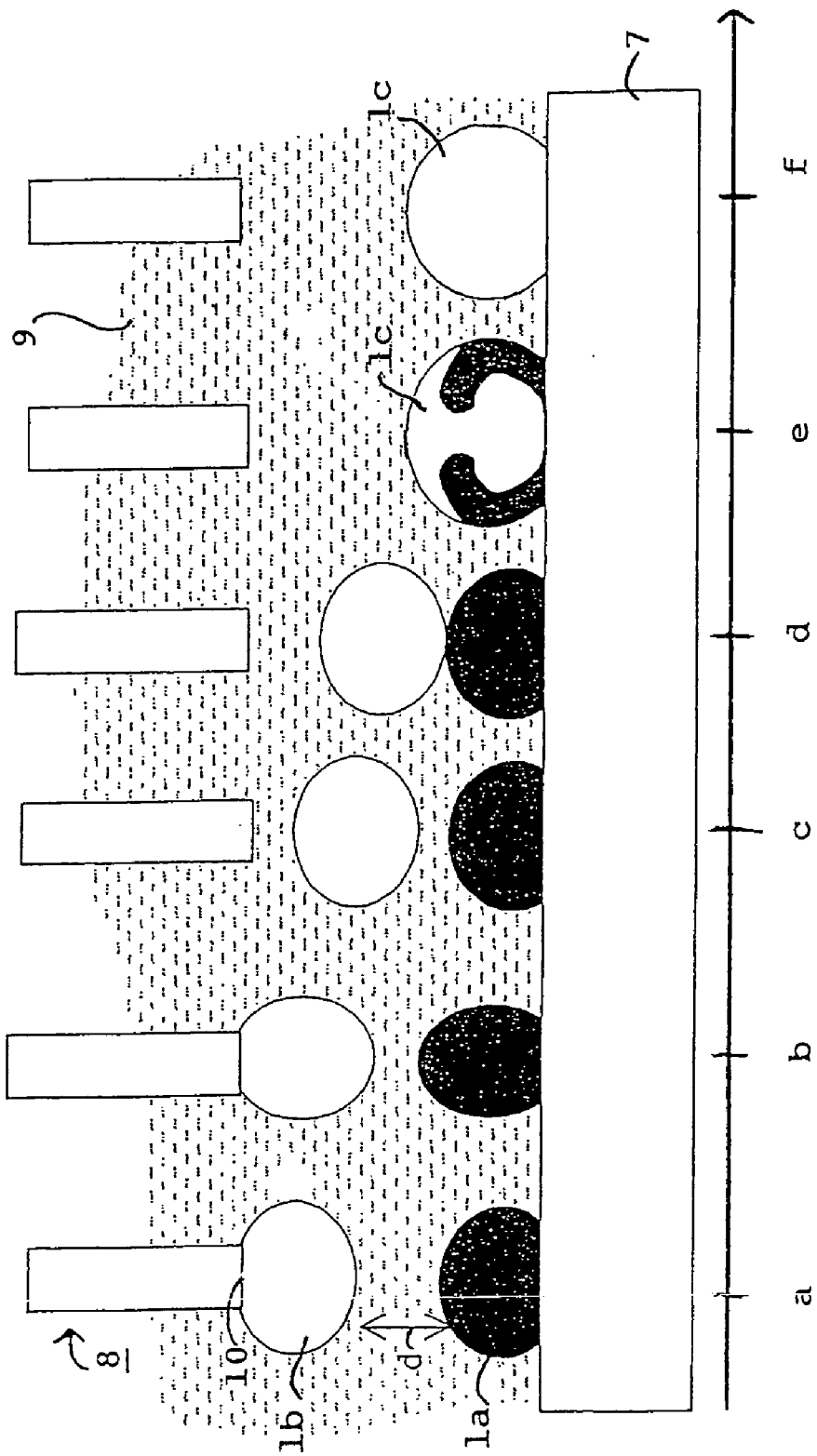

FIG. 7 represents the progression versus time of the mixing process of the first and second drops 1a and 1b in a viscous liquid 9 when the outlet orifice 10 of the injector 8 is arranged in such a way that the distance d between the first and second drops 1a and 1b is smaller than or equal to the mean diameter of the second drop, considering that the second drop is substantially round when it forms at the outlet orifice 10. Thus the mean diameter is about one millimetre for a 0.25 µl drop. The injection and mixing process of the droplets 1a and 1b is represented at different times a to h, the lapse of time necessary to go from one time to the next between the times a and g being about one millisecond.

At the time a, the first and second drops are separated by a distance d smaller than or equal to the mean diameter of the drops. The electrostatic forces applied after formation of the second drop 1b deform the first and second drops 1a and 1b, the latter attracting one another as represented at the time b. The two drops then present, at the time c, a conical shape, favouring their contact, unlike the case described in FIG. 5 where a dimple appears opposing the coalescence phenomenon. Thus, the attraction forces of the two drops 1a and 1b being elastic, they deform the interfaces of the two drops 1a and 1b by their mode of action so as to eliminate the existence of a dimple, which modifies the drainage of the environment favourably. The reagent of the second drop 1b then flows into the reagent of the first drop 1a, at the time d, the reagent of the second drop 1b penetrating to the centre of the first drop 1a, which results in a flow of the reagent of the first drop 1a at the circumference of the new drop in formation 1c (represented at the time d).

The new drop 1c is then detached from the injector before the reagent of the first drop rises to the level of the outlet orifice 10 of the injector 8 (represented at the time e). There is therefore no contact between the injector and the reagent of the first drop 1a, thus preventing any possible contamination. Coiling fostering mixing of the two reagents takes place in the new drop 1c, at the time f. After fusion, the new drop 1c takes a definitively round shape and the natural diffusion phenomenon ensures mixing of the two reagents represented at the time g and, after a few seconds, the mixture is uniform as represented at the time h.

It is possible to accelerate the mixing process by imposing a second voltage impulse between the first and second electrodes 17 and 18, during a second preset time period of about a few milliseconds for example. The second voltage impulse is preferably imposed at a time corresponding to the time g. The appearance of superficial charges at the interface of the new drop 1c creates a flow outside and inside the new drop 1c. The flow renders the content of the new drop 1c uniform in a few milliseconds to a few seconds.

FIG. 8 represents the progression versus time of the mixing process of the first and second drops 1a and 1b in a viscous liquid 9, when the outlet orifice 10 of the injector 8 is arranged so that the distance d is greater than the mean diameter of the second drop 1b. After formation of the second drop 1b, at the time a, a first voltage impulse is applied between the first and second electrodes, resulting in deformation of the first and second drops 1a and 1b, as represented at the time b. The second drop 1b is then detached from the injector 8 (time c) and falls freely into the viscous liquid 9 before coming into contact with the first drop 1a (time d).

The phenomenon described in FIG. 7 is then reproduced, the second drop 1b penetrating into the first drop 1a (time e), which results in a flow of the reagent of the first drop 1a at the circumference of the new drop in formation 1c. The coalescence phenomenon between the first and second drops 1a and 1b is instantaneous and reproducible, the time lapse between the time d and the time e being only 10 milliseconds. The mixture is uniform after a few seconds (time f).

As described above, a second voltage impulse can be applied to accelerate the phenomenon of mixing of the reagents of the first and second drops 1a and 1b inside the new drop 1c by convection. The velocity of the second drop 1b during its fall is about a few mm/s to a few cm/s. In this case, there is no contact between the injector 8 and the first drop 1a, and no risk of contamination of the injector by the reagent of the first drop 1a.

The injection and mixing device according to the invention presents the advantage of preventing the occurrence of a dimple such as the one described in the embodiment of FIG. 5, the dimple tending to delay or even inhibit coalescence in a viscous liquid environment. The device also enables efficient control of the volume of the second drop 1b injected by means of the volumetric pump, the volume being independent from the voltage applied, from the geometry of the injector and from the distance between the two electrodes. The mixing and injection process is also reproducible, as the hydrodynamic phenomena occurring are themselves reproducible.

The device does not present any risk of contamination of the injector either. For critical mixing and analysis processes, in the medical diagnosis field for example, the outlet orifice 10 of the injector 8 should preferably be placed at a distance such that the distance d is greater than the mean diameter of the second drop, whereas for less critical processes, the injector can be placed closer to the first drop, without any fear of contamination.

Figure 9:
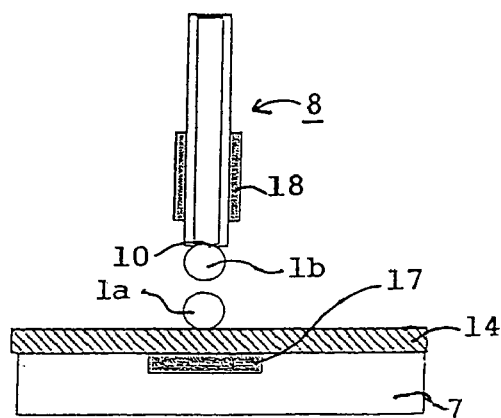
FIGS. 9 to 14 schematically represent various embodiments of an injection and mixing device according to the invention.

According to a particular embodiment, represented in FIG. 9, the analysis support 7 is formed by an insulating material, such as a ceramic, glass or a polymer and is provided with an electrically conducting zone forming the first electrode 17. The electrically conducting zone can be achieved by conventional micro-technology techniques. Thus, for example, the second electrode 17 can be achieved by photolithography on a layer of gold. The electrically insulating layer 14, on which the first drop 1a is deposited is preferably made of resin, oxide ($SiO_2$) or silicon nitride ($Si_3N_4$).

In FIG. 9, the injector 8, connected to the volumetric pump (not shown), comprises, at its free end, a capillary pump which is preferably a micro-tube made of fused silica, sheathed with polyimide. The outlet orifice 10 of the injector 8 is preferably formed by one of the ends of the capillary, the other end being connected to the volumetric pump. The capillary has a diameter of about a few microns to a few hundred microns, the volume of the first and second drops being about a few tens of nanolitres to a few hundred nanolitres. The first and second drops can have different volumes, depending on the injection mode chosen for the first drop.

The second electrode 18 preferably surrounds a part of the walls of the injector 8 and can notably be made from an electrically conducting material, sheathed on the walls of the injector 8.

In a particular embodiment, the capillary constituting a part of the injector is fitted in a metal tube forming the second electrode, which presents the advantage of being easy to implement and of being compatible with a large number of biological and chemical analysis processes. The second electrode is in fact never in contact with the reagents of the first and second drops 1a and 1b, which prevents the occurrence of air bubbles able to result from electrolysis phenomena.

Figure 10:
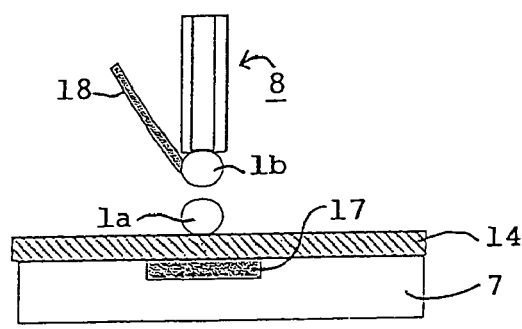

According to another embodiment represented in FIG. 10, the second electrode 18 is a metal needle placed near the outlet orifice 10 of the injector 8. The metal needle is for example a gold, aluminium or platinum thread. It can be covered with Parylene®, i.e. a polymer film coming from a dimer of di-para-xylylene or Teflon® type, to avoid certain biocompatibility problems.

Figure 11:
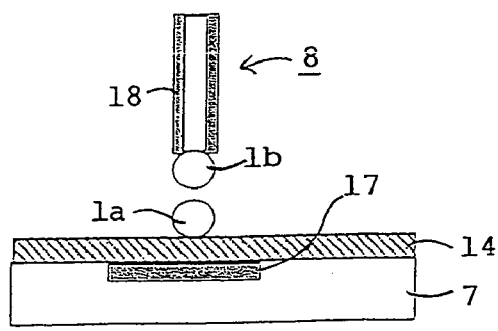

In FIG. 11, the injector 8 formed by a capillary is stuck to a conducting micro-tube forming the second electrode 18. The conducting micro-tube can be made of aluminium for example. The capillary forming the injector can also be covered by a metal layer, for example of platinum or gold.

Figure 12:
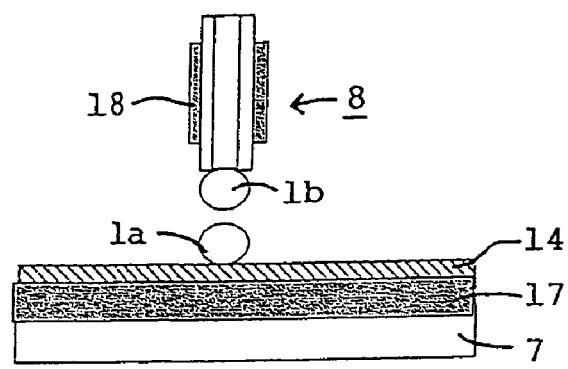

According to another embodiment, represented in FIG. 12, the first electrode 17 is formed by at least one electrically conducting layer arranged between the insulating analysis support 7 and the insulating layer 14.

The injection and mixing device can also comprise a plurality of injectors 8, in order to inject either successively a plurality of second drops containing different reagents into a single first drop, or simultaneously a plurality of second drops, able to contain a single reagent, into a plurality of first drops able to contain a single reagent. Thus, in FIG. 13, a row of seven first drops 1a is arranged on the electrically insulating layer 14, so that seven injectors 8, arranged above each first drop 1a, each inject a second drop 1b simultaneously into each first drop 1a.

Each injector comprises a second electrode 18. In a first variant, the first electrode 17 can be common to the seven first drops 1a, i.e. it is formed by an electrically conducting zone formed by a continuous strip 20 arranged under the row of first drops 1a (left part of FIG. 13). In another variant, each first drop is arranged on a first electrode 17, formed by an electrically conducting zone (right part of FIG. 13).

Figure 14:
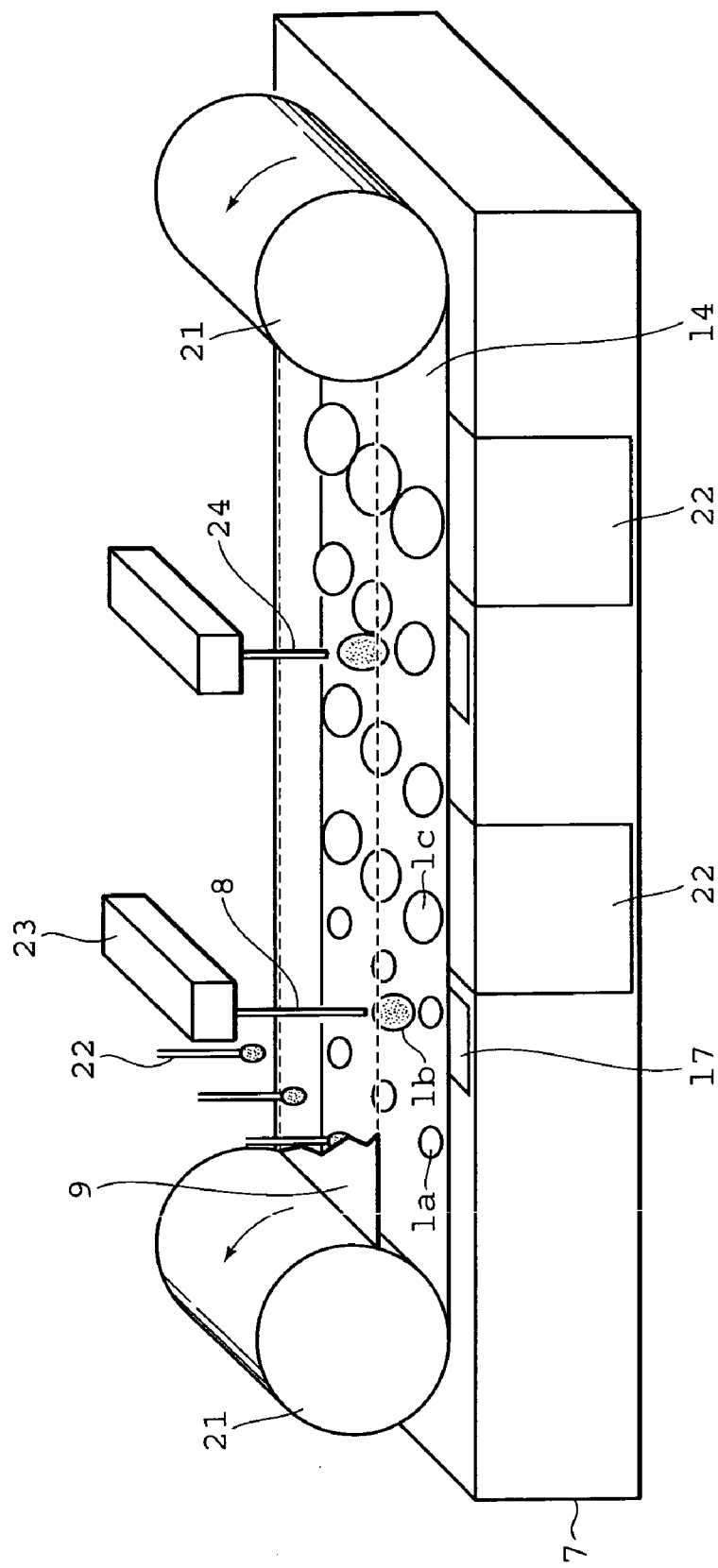

According to another particular embodiment, as represented in FIG. 14, the injection and mixing device enables a large number of mixings of reagents, and also thermal treatments, to be performed in parallel. The analysis support 7 is covered by an electrically insulating layer 14, on which a row of first drops 1a is deposited by capillaries 22. The capillaries 22 preferably deposit first drops 1a constituted by different reagents on the electrically insulating layer 14.

The electrically insulating layer 14 is preferably a flexible film, for example made of polycarbonate with a thickness of 50 μm, the film being covered by a layer of oil 9. The insulating film moves due to the rotation of two coils 21. The analysis support 7 preferably comprises the temperature control means situated at preset locations 22, enabling different thermal treatments to be applied when the drops 1a and 1b pass over these locations.

Figure 13:
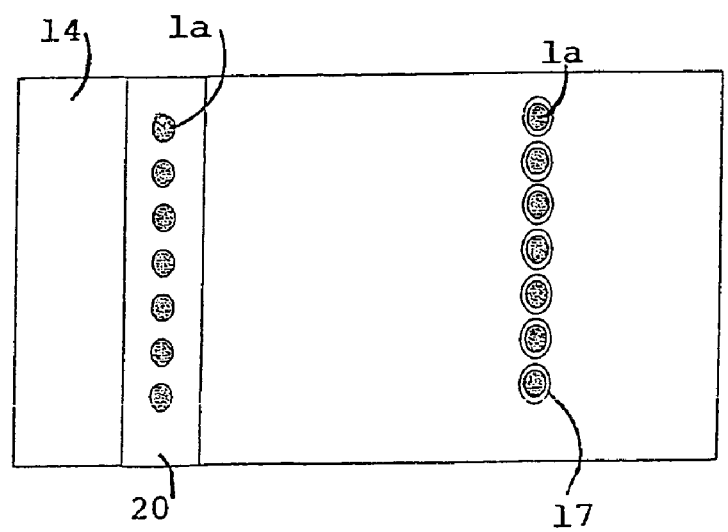

An injector 8, above each first drop 1a, forms a second drop 1b comprising a different reagent from the reagents of the first drops 1a. The injector is fixed to a robot 23 which performs movement of the injector 8 and enables it to be successively positioned above each first drop 1a of the row. After formation of the drop 1b, a voltage impulse is applied between the first and second electrode to foster the coalescence phenomenon and formation of a new drop 1c. As represented in FIG. 13, the first electrode 17 can be common to the row of first drops 1a or be arranged under each first drop 1a of the row.

It is then possible to mix the reagent of the second drops 1b with each reagent of each first drop 1a, without contaminating the injector with the different reagents of the first drops 1a in which the injector has already injected a second drop 1b, which presents the advantage of not having to rinse the injector after each mixing.

A second injector 24, of the same type as the injector 8, can also be fitted, so as to mix another reagent with the row of new drops 1c formed. The device presents the advantage of being able to speed up or slow down the mixing process according to the speed of injection and formation of the second drops, the speed of movement of the insulating film 14 and that of the injectors 8 and 24.

The reagents respectively forming the first and second drops can, for example, contain biological molecules, such as DNA, proteins or living organisms.

The invention claimed is:

1. A device for injection and mixing of droplets of respective first and second liquid reagents, comprising:
    an analysis support including an electrically insulating layer;
    a viscous liquid deposited on the electrically insulating layer, wherein said viscous liquid is immiscible with said reagent droplets within said viscous liquid;
    a droplet of said first reagent deposited on said electrically insulating layer within the viscous liquid;
    an injector including said second liquid reagent and an outlet orifice, said injector forming a droplet of said second liquid reagent above the said droplet of first reagent;
    a first electrode arranged underneath said droplet of first reagent and said electrically insulating layer;
    a second electrode arranged near to the outlet orifice of the injector; and
    a controller for applying and controlling a voltage applied between said first and second electrodes, said voltage generating electrostatic forces which cause a formation of said droplets of respective first and second reagents, before said droplets come into contact and mix.

2. Device according to claim 1, wherein the second electrode is a metal needle.

3. Device according to claim 1, wherein the second electrode surrounds a part of the walls of the injector.

4. Device according to claim 3, wherein the injector is sheathed by an electrically conducting material forming the second electrode.

5. Device according to claim 1, wherein the injector comprises free end further including a capillary tube connected to a volumetric pump.

6. Device according to claim 5, wherein the capillary tube is a micro-tube made of fused silica, sheathed with polyimide.

7. Device according to claim 1, wherein the electrically insulating layer of the analysis support is arranged on an electrically insulating support provided with an electrically conducting zone forming the first electrode.

8. Device according to claim 7, wherein said zone is formed by at least one electrically conducting layer arranged between the insulating layer and the electrically insulating support.

9. Device according to claim 7, wherein said zone is formed by a continuous strip arranged under a row of first drops.

10. Device according to any claim 1, wherein the electrically insulating layer of the analysis support is mobile.

11. Device according to claim 1, comprising a plurality of injectors arranged so as to simultaneously form second drops above a row of first drops.

12. Device according to claim 1, comprising a plurality of injectors arranged so as to successively form second drops.

13. Device according to claim 1, wherein the controller places the first and second electrodes at the same potential during formation of the second drop by the injector, and applies, after formation of the second drop, a first voltage impulse between the first and second electrodes during a first time period of about a few milliseconds to one second.

14. Device according to claim 1, wherein the controller applies a second voltage impulse between the first and second electrodes during a second time period of about a few milliseconds to a few seconds, after the first impulse.

15. Device according to claim 1, wherein the outlet orifice of the injector is arranged so that a distance between the first drop and the second drop is smaller than or equal to the mean diameter of the second drop.

16. A process for mixing of droplets of respective first and second liquid reagents, comprising:
    depositing a viscous liquid on an electrically insulating layer of an analysis support, wherein said viscous liquid is immiscible with said reagent droplets within said viscous liquid;
    depositing a droplet of said first reagent on said electrically insulating layer within the viscous liquid;
    forming a droplet of said second liquid reagent above the said droplet of first reagent, said droplet being formed via an outlet orifice of an injector;
    arranging a first electrode underneath said droplet of first reagent and said electrically insulating layer;
    arranging a second electrode near to said outlet orifice; and
    applying and controlling a voltage between said first and second electrodes, said voltage generating electrostatic forces which cause a deformation of said droplets of respective first and second reagents before said droplets come into contact and mix.

* * * * *